United States Patent [19]

McClure

[11] 3,934,980

[45] Jan. 27, 1976

[54] METHOD OF ASSAY FOR PROSTAGLANDINS OF THE E SERIES

[75] Inventor: William O. McClure, So. Pasadena, Calif.

[73] Assignee: Nelson Research & Development Co., Irvine, Calif.

[22] Filed: Oct. 7, 1974

[21] Appl. No.: 512,448

[52] U.S. Cl. .................................. 23/230 B; 424/7
[51] Int. Cl. ...................... G01n 21/00; G01n 31/08; G01n 33/16
[58] Field of Search ....................... 23/230 B; 424/7

[56] References Cited
OTHER PUBLICATIONS

N. Ambache et al., Brit. J. Pharmacol. 33, 162, (1968).
E. W. Horton, Physiological Review, 49, 122, (1969).
N. H. Anderson, Chem. Abstr. 71, 27642p, (1969).
E. Änggärd et al., J. Chromatogr., 48, 542, (1970).

*Primary Examiner*—Robert M. Reese
*Attorney, Agent, or Firm*—Martin A. Voet

[57] ABSTRACT

A method for assaying prostaglandins of the E series by reacting a compound of this series with $NaB^3H_4$, isolating the tritiated prostaglandin and measuring its radioactivity.

9 Claims, No Drawings

METHOD OF ASSAY FOR PROSTAGLANDINS OF THE E SERIES

BACKGROUND OF THE INVENTION

1. Field of the Invention

The present invention relates to an assay. More particularly, the present invention relates to an assay for prostaglandins of the E series.

2. Background of the Prior Art

Prostaglandins of the E series are characterized by containing one $C_{11}$ hydroxy group and one $C_9$ keto group in the cyclopentane ring. For example, prostaglandin $E_2$ ($PGE_2$) is a compound having the following structural formula

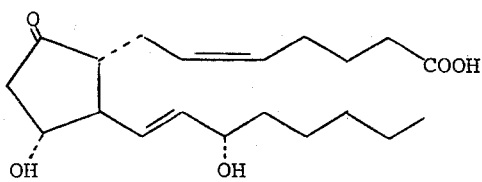

Prostaglandins of the E series exist in the cells of many, if not all animals. The exert biological activities in the body of the animal in which it is present. A simple assay for the presence of prostaglandins of the E series would be valuable for research and diagnostic purposes.

SUMMARY OF THE INVENTION

The present invention relates to a method for assaying prostaglandins of the E series comprising reacting prostaglandins of the E series with sodium borotritide in a suitable solvent, isolating the tritiated prostaglandin and measuring its radioactivity.

The following general reaction is utilized by the present assay method, as shown for prostaglandin $E_2$:

The reduction reaction of the sodium borotritide and $PGE_2$ takes place by reacting an excess of sodium borotritide in a suitable solvent, for example, alcohols, such as, for example, methanol, ethanol, propanol, isopropanol, etc. and water, at temperatures between about 0°–75°C and preferably about 20°–30°C for a period of time sufficient to complete the reaction. Reaction time generally varies from 0.1–10 hours and preferably 0.1–2 hours.

The tritiated prostaglandin (in this case prostaglandin $F_{2\alpha}$ and $F_{2\beta}$) are then isolated from the reaction mixture by any suitable analytical method including thin layer chromatography (TLC), paper chromatography, column chromatography, etc. and preferably TLC. The isolated, tritiated prostaglandins are then evaluated for radioactivity by conventional scintillation techniques.

The foregoing method results in a qualitative as well as quantitative assay for $PGE_2$.

This assay may be used to determine levels of prostaglandins of the E series in various biological systems including biological tissues, blood, urine, etc. In order to guard against loss of a prostaglandin E in a sample, e.g. by degradation, an internal standard can be used. For example, a known amount of $^{14}C$ labeled $PGE_2$ may be added to the sample prior to the assay and counted at the end of the procedure. The percent reduction of $^{14}C$ $PGE_2$ from the known amount placed in the sample indicates the percent of $PGE_2$ lost during the assay procedure. Other similar internal standards may be used.

In order to minimize interference of background radiation caused by exchange of $^3H$ atoms for $^1H$ atoms in water present in the assay sample, the water remaining in the reaction sample is preferably removed by any convenient method, e.g. a deliquescent substance such as magnesium sulfate can be added to the sample.

The following Examples are for the purpose of illustration and it is understood that the invention is not to be limited to the reagents or conditions set forth.

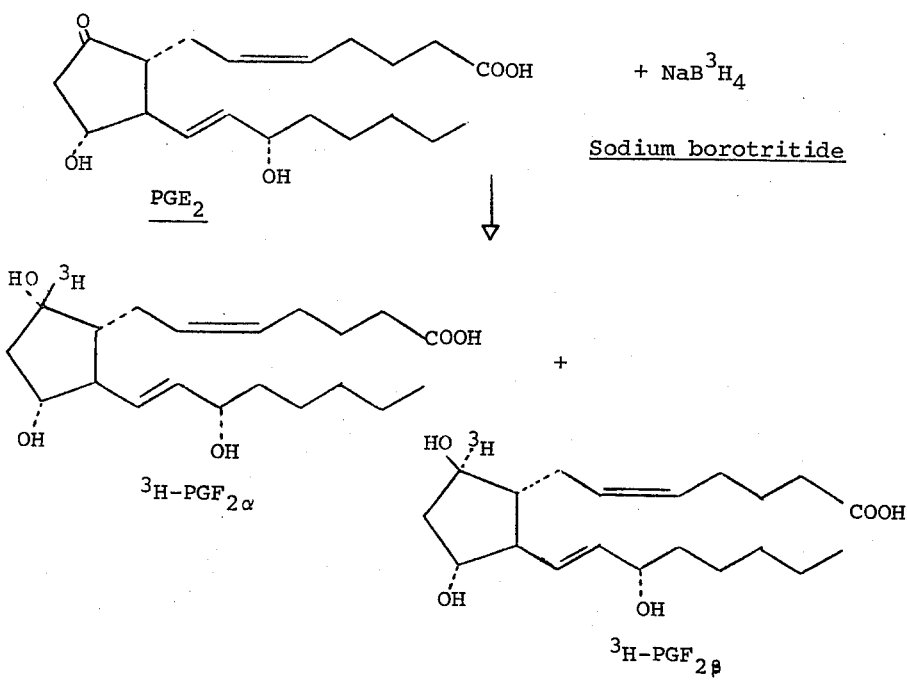

EXAMPLE I

Assay for $PGE_2$ is conducted by reacting $10^{-9}$ g sodium borotritide (20 C/m-mole) with $10^{-10}$ g $PGE_2$ at 50°C in anhydrous methanol for 30 minutes. The reaction mixture is spotted on silica gel TLC plates and developed in a solvent system consisting of the organic phase of ethyl acetate-iso-octane-glacial acetic acid-water in ratios of 110:50:20:100. The TLC plates are visualized with iodine vapor and the reaction product scraped. The radioactivity is measured by a standard scintillation counter. The results indicate that in excess of 90% of the $PGE_2$ is recovered.

EXAMPLE II

EXAMPLE I is repeated in the presence of prostaglandin $F_{2\alpha}$ ($PGF_{2\alpha}$). No interference of the reaction by $PGF_{2\alpha}$ is found.

I claim:

1. A method for assaying for prostaglandins of the E series comprising reacting prostaglandins of the E series with sodium borotritide in a suitable solvent, isolating the tritiated prostaglandins, and measuring the amount of radioactivity of the isolated tritiated prostaglandins.

2. The method of claim 1 wherein the solvent is an alcohol or water.

3. The method of claim 1 wherein the prostaglandin is prostaglandin $E_2$.

4. The method of claim 1 wherein an internal standard is used.

5. The method of claim 1 having the additional step of removing any water present in the reaction mixture before isolating the tritiated prostaglandins.

6. The method of claim 1 wherein the tritiated prostaglandins are isolated by thin layer chromatography.

7. A method for assaying prostaglandin $E_2$ comprising reacting a biological sample containing prostaglandin $E_2$ with sodium borotritide in a suitable solvent, removing the water in the reaction product, isolating the tritiated prostaglandins by thin layer chromatography and measuring the amount of radioactivity of the isolated tritiated prostaglandins.

8. The method of claim 7 wherein an internal standard is used.

9. The method of claim 8 wherein the internal standard is $^{14}C$ labeled prostaglandin $E_2$.

* * * * *